(12) United States Patent
Vitiello et al.

(10) Patent No.: US 10,246,781 B2
(45) Date of Patent: Apr. 2, 2019

(54) METHOD FOR REMOVING A METAL DEPOSIT PLACED ON A SURFACE IN A CHAMBER

(71) Applicant: KOBUS, Montboonot-Saint-Martin (FR)

(72) Inventors: Julien Vitiello, Grenoble (FR); Jean-Luc Delcarri, Saint Ismier (FR); Fabien Piallat, Montbonnot-Saint-Martin (FR)

(*) Notice: Subject to any disclaimer, the term of this patent is extended or adjusted under 35 U.S.C. 154(b) by 0 days.

(21) Appl. No.: 15/328,413

(22) PCT Filed: Jul. 24, 2015

(86) PCT No.: PCT/EP2015/067044
§ 371 (c)(1),
(2) Date: Jan. 23, 2017

(87) PCT Pub. No.: WO2016/012610
PCT Pub. Date: Jan. 28, 2016

(65) Prior Publication Data
US 2017/0204522 A1    Jul. 20, 2017

(30) Foreign Application Priority Data

Jul. 24, 2014  (FR) ...................... 14 57137

(51) Int. Cl.
*C23F 1/00*  (2006.01)
*C07C 49/167*  (2006.01)
(Continued)

(52) U.S. Cl.
CPC ................ *C23F 1/00* (2013.01); *C07C 45/00* (2013.01); *C07C 49/167* (2013.01);
(Continued)

(58) Field of Classification Search
CPC ......... C23F 1/00; C07C 49/167; C07C 45/00; C23G 5/00; C23C 16/4405; C23C 14/564; H01J 37/32862
See application file for complete search history.

(56) References Cited

U.S. PATENT DOCUMENTS

| | | | |
|---|---|---|---|
| 2001/0009154 A1* | 7/2001 | Nguyen .............. | C23C 16/4405 134/1 |
| 2005/0224456 A1 | 10/2005 | Chen et al. | |
| 2011/0259366 A1* | 10/2011 | Sweeney ................. | C23C 14/48 134/10 |

FOREIGN PATENT DOCUMENTS

DE    102011056538 A1    6/2013

OTHER PUBLICATIONS

Diffusion in Solids Simple Diffusion (found on the internet site https://nanohub.org/resources/5949/download/ch06_diffusion.pdf)(2013).*

(Continued)

*Primary Examiner* — Nadine G Norton
*Assistant Examiner* — Mahmoud Dahimene
(74) *Attorney, Agent, or Firm* — Burr & Forman LLP; Harvey S. Kauget

(57) ABSTRACT

A method for removing a metallic deposit disposed on a surface in a chamber, including the following steps:
  a) a step of oxidizing the metallic deposit;
  b) a step of injecting chemical species adapted to volatilized the oxidized metallic deposit, the step b) being implemented during at least a part of step a); and
  in step b), the chemical species are injected according to a sequence of pulses.

15 Claims, 2 Drawing Sheets

(51) Int. Cl.
  *C07C 45/00* (2006.01)
  *C23C 14/56* (2006.01)
  *C23C 16/44* (2006.01)
  *C23G 5/00* (2006.01)
  *H01J 37/32* (2006.01)

(52) U.S. Cl.
  CPC ........ *C23C 14/564* (2013.01); *C23C 16/4405* (2013.01); *C23G 5/00* (2013.01); *H01J 37/32862* (2013.01)

(56) References Cited

OTHER PUBLICATIONS

French Search Report from French Patent Application No. 1457137, dated Mar. 23, 2015.
International Search Report from International Patent Application No. PCT/EP2015/067044, dated Oct. 6, 2015.
Sekiguchi et al. "Reaction of Copper Oxide and β-Diketone for In situ Cleaning of Metal Copper in a Copper Chemical Vapor Deposition Reactor", Japanese Journal of Applied Physics (2000), 39(11), pp. 6478-6486.

* cited by examiner

METHOD FOR REMOVING A METAL DEPOSIT PLACED ON A SURFACE IN A CHAMBER

BACKGROUND

The present invention relates to a method for removing a metallic deposit placed on a surface in an enclosure.

A method for removing a metallic deposit on a surface of an enclosure, known in the state of the art, comprises the following steps:
  a) a step of oxidizing the metallic deposit;
  b) a step of injecting chemical species adapted to volatilize the oxidized metallic deposit, said step b) being implemented during at least a part of step a).

However, such a removal method is not satisfactory.

In fact, the chemical species adapted to volatilize the oxidized metallic deposit can also react with the metallic deposit before the oxidation of the latter. Step a) is thereby blocked.

Thus, the reaction of the chemical species with the metallic deposit interferes with the removal method, and above all adversely affects its effectiveness.

In particular, this is the case when the removal method is carried out in order to remove a deposit of copper (Cu) on a surface in an enclosure. Step a) generally comprises the introduction of gaseous oxygen or gaseous ozone. The chemical species adapted to volatilize the copper oxide comprise hexafluoroacetylacetone (hfacH). When it is injected into the enclosure, the chemical species hfacH also reacts with the copper before the latter is oxidized. The oxidation reaction is then blocked.

The subject of the present invention is therefore to propose a method for removing a metallic deposit making it possible to limit the parasitic reactions capable of blocking said method.

A first application of the invention relates to cleaning off metallic residues deposited on the inner walls of a deposition chamber.

Another application of the invention relates to the manufacture of printed circuits, and more particularly the etching of metallic layers used in particular for filling vias, which are metalized holes allowing the electrical connection between several layers of a printed circuit.

Conventionally, the vias are filled in excess with a metal such as copper, so as to ensure a satisfactory filling of the vias. The excess metal is removed by a step of chemical mechanical etching. A barrier layer is disposed between the substrate of the printed circuit and the layer of metallic deposit, in order to control the thickness of the etching. The chemical mechanical etching step requires the use of barrier layers so as to ensure a very precise control of the method and moreover requires subsequent operations of cleaning the etched surface, which is complex and expensive.

Another subject of the invention is to propose a method for manufacturing metalized vias that is simplified and less expensive.

SUMMARY

The present invention aims to completely or partially overcome the aforementioned drawbacks and relates to a method for the removal of a metallic deposit placed on a surface in a chamber, said method comprising the following steps:
  a) a step of oxidizing the metallic deposit;
  b) a step of injecting chemical species capable of volatilizing the oxidized metallic deposit, said step b) being implemented during at least a part of step a);
  said removal method being noteworthy in that in step b), the chemical species are injected according to a sequence of pulses.

Thus, the injection, according to a sequence of pulses, of the chemical species adapted to volatilize the oxidized metallic deposit makes it possible to avoid the parasitic reaction comprising the reaction of the metallic deposit disposed on a surface in an enclosure with said chemical species.

Furthermore, the injection, according to a sequence of pulses, of the chemical species adapted to volatilize the oxidized metallic deposit also makes it possible to limit the quantity of said chemical species.

According to an embodiment, in step b), during the latest pulse of two successive pulses, the chemical species are injected in a sub-stoichiometric quantity with respect to the quantity of the oxidized metallic deposit between said two successive pulses.

Thus, it is possible to limit the consumption of the chemical species capable of volatilizing the oxidized metallic deposit, and consequently to limit the cost of removal of the deposit.

According to an embodiment, the sequence of pulses of the chemical species adapted to volatilize the oxidized metallic deposit is periodic.

According to an embodiment, the period of the sequence of pulses is less than 1 second.

According to an embodiment, the enclosure is maintained at a temperature comprised between 20 and 250° C., preferably between 20 and 150° C.

According to an embodiment, step a) is carried out by injecting an oxidizing species comprising at least one of the following species: oxygen, ozone, nitrous oxide.

According to an embodiment, the chemical species injected in step b) comprise hexafluoroacetylacetone.

According to an embodiment, the metallic deposit comprises at least one of the following elements: Copper, Titanium, Tantalum, Ruthenium, Zinc, Zirconium, Vanadium, Silver, Gold, Chromium.

According to an embodiment, the first pulse of step (b) is implemented after the start of step a).

According to an embodiment, the method is implemented for cleaning off metallic residues disposed on the inner walls of a deposition chamber.

According to an embodiment, the method is implemented for etching a metallic deposit deposited in excess on a surface.

Optionally, before steps a) and b), a mask is affixed in a localized manner onto the metallic deposit.

According to an embodiment, the method comprises the following steps:
  the mask is affixed over each region of the metallic deposit to be retained;
  steps a) and b) are implemented in order to remove the excess of the metallic deposit in each region not covered by the mask.

According to another embodiment, the method comprises the following steps:
  the mask is affixed over each region of the metallic deposit to be etched;
  chemical species adapted to passivate the metallic deposit in each region not covered by the mask are injected;
  the mask is removed;

steps a) and b) are implemented in order to remove the excess metallic deposit in each region covered beforehand by the mask.

According to an embodiment, steps a) and b) are repeated as many times as necessary in order to remove the excess metallic deposit.

BRIEF DESCRIPTION OF THE DRAWINGS

The invention will be better understood in light of the following description of specific and non limitative embodiments of the invention with reference to the attached figures in which.

DETAILED DESCRIPTION

For the different embodiments, the same references will be used for elements that are identical or providing the same function, for the sake of simplifying the description.

Figure 1:
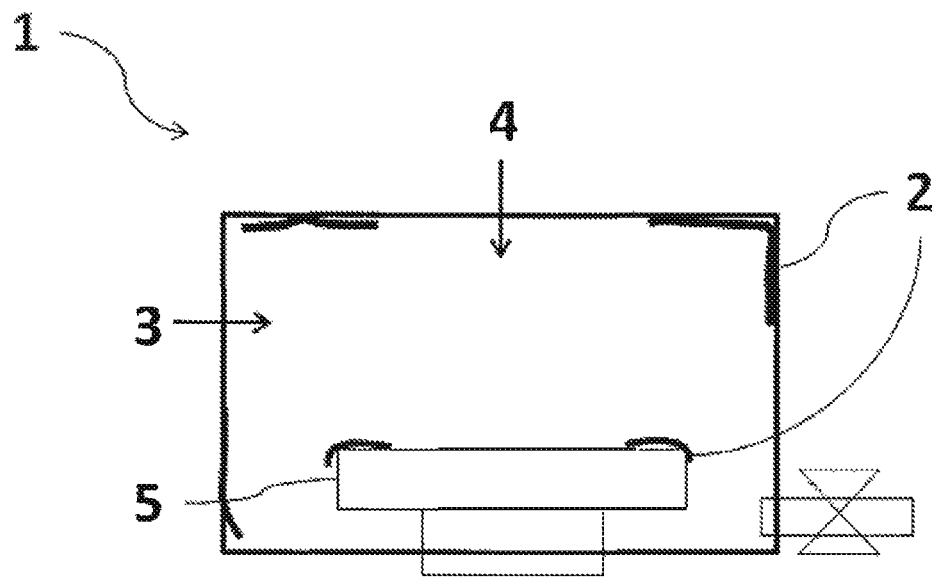
FIG. 1 is a diagrammatic presentation of an enclosure.

FIG. 1 shows a enclosure 1 in which a support 5 is disposed.

An unwanted metallic deposit 2 is observed on surfaces in the enclosure 1, namely on the inner walls of the enclosure 1, as well as on the support 5.

The metallic deposit 2 can comprise at least one of the following elements: Copper, Titanium, Tantalum, Ruthenium, Zinc, Zirconium, Vanadium, Silver, Gold, Chromium.

The method for removing the metallic deposit 2 on the surfaces in the enclosure 1 comprises a step a) of oxidizing the metallic deposit 2.

Step a) can be carried out by the injecting oxidizing species in gaseous form by an injection system 3.

Step (a) can be carried out by the injecting oxidizing species comprising at least one of the following species: oxygen, ozone, nitrous oxide.

Figure 2:
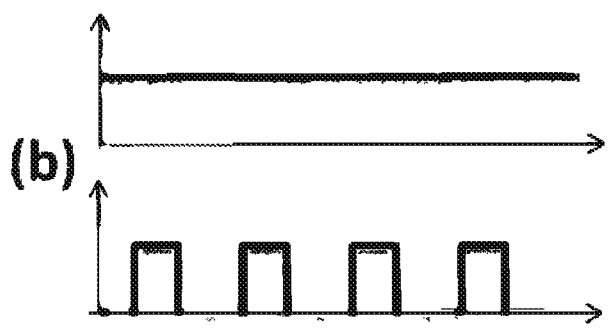
FIG. 2(a) shows the quantity of oxidizing species injected into the enclosure as a function of time according to an embodiment of the invention.
FIG. 2(b) shows the quantity of chemical species adapted to volatilize the oxidized metallic deposit injected into the chamber as a function of time according to an embodiment of the invention, the time scale being the same as that of FIG. 2(a)

The oxidizing species can be injected continuously throughout the whole duration of the cleaning process as shown in FIG. 2(a).

The oxidizing species can be injected in a constant flow.

During the injection of the oxidizing species, an oxidation reaction of the metallic deposit 2 takes place on their free surface.

The removal method also comprises a step b) of injecting chemical adapted to volatilize the oxidized metallic deposit, said step b) taking place at least partially during the oxidation process, but starting after the start of step a);

However, the chemical species adapted to volatilize the oxidized metallic deposit could equally well react with the metallic deposit 2, and thus passivate the exposed surface of said deposit. This passivation reaction of the metallic deposit 2 is a parasitic reaction which limits or blocks any oxidation reaction of said deposit by the oxidizing species.

In order to avoid this parasitic reaction, the chemical species adapted to volatilize the oxidized metallic deposit are injected, in step (b), according to a sequence of pulses (as shown in FIG. 2(b)), by an injection system 4. Although the pulses shown in FIG. 2b have a square-wave shape, other shapes of pulses can be envisaged, provided that two successive pulses are separated by a time interval during which no chemical species adapted to volatilize the oxidized metallic deposit is injected.

The enclosure 1 can be maintained at a temperature comprised between 20 and 250° C. so as to maintain in gaseous form the chemical species capable of volatilizing the metallic deposit. Preferably, the temperature of the enclosure 1 is maintained at a temperature comprised between 20 and 150° C., yet more preferably between 20 and 100° C.

In order to optimize the removal method, the oxidizing species are injected from the start of the removal process in order to oxidize the metallic deposit 2 at least at the level of its free surface.

Thus, a layer of oxidized metallic deposit covers the metallic deposit 2.

Advantageously, the first pulse of step b) is implemented after the start of step a).

It may be advantageous to know the oxidation kinetics of the metallic deposit 2.

The oxidation kinetics of the metallic deposit 2 depends on its nature and on the conditions of its formation, but also on the oxidation conditions of step a).

However, it is within the capabilities of a person skilled in the art to empirically determine the oxidation kinetics of the metallic deposit 2.

In this respect, a person skilled in the art may refer to the document Guangwen Zhou et al., J. Mater. Res., Vol. 20, No. 7 (1684-1694), July 2005.

Thus, before the implementation of the method for the removal of the metallic deposit 2 on a surface in the enclosure, it is advantageous to determine the oxidation kinetics of the metallic deposit for different oxidation conditions, and draw up charts for each of the types of metallic deposit 2 capable of being deposited on a surface in the chamber 1.

Said charts can then be used to determine the quantity of the oxidized metallic deposit for a predetermined duration and under given oxidation conditions.

Therefore, for the implementation of the method for removing the metallic deposit 2 on a surface in the enclosure 1, the use of said charts makes it possible to determine the quantity of the oxidized metallic deposit in step a) for a given duration.

Throughout the whole duration of the first pulse of the sequence of pulses in step b), the layer of oxidized metallic deposit is, at least partially, volatilized by the chemical species.

Once said first pulse has ended, the process starts again, the oxidizing species are again in the majority in the enclosure 1, and consequently the oxidation reaction of the metallic deposit 2 is the dominant reaction, until the start of the next pulse of the sequence of pulses of step b).

Advantageously, the duration of the pulses of the sequence of pulses is set so that the layer of the oxidized metallic deposit is not entirely volatilized. Therefore, the portion of the layer of the oxidized metallic deposit remaining forms a barrier to passivation of the metallic deposit 2 by the chemical species injected in step b). The passivation reaction is thus blocked.

In other words, in the course of the injection of the chemical species for volatilizing the oxidized metallic deposit, during the later of two successive pulses, the chemical species are injected in a sub-stoichiometric quantity with respect to the quantity of the oxidized metallic deposit between said two successive pulses.

The aforementioned sub-stoichiometric quantity can be determined by the knowledge both of the quantity of the metallic deposit oxidized in step a) between two pulses of the sequence of pulses of step b), and the mechanism of volatilization reaction of said oxidized metallic deposit with the chemical species.

The mode of injection of chemical species adapted to volatilize the oxidized metallic deposit therefore has numerous advantages.

The first advantage is to make the removal method according to the invention efficient. In fact, the parasitic reaction comprising the passivation of the metallic deposit 2 by the chemical species injected is thus neutralized. The neutralization of said parasitic reaction avoids having to open the enclosure 1, and having to resort to a process for decontaminating the latter.

The second advantage is the ability to control the quantity of chemical species injected in step b), and thus make it possible to reduce the cost of the removal method.

Furthermore, the sequence of pulses in step b) can be periodic.

Moreover, the sequence of pulses of step b) can have a period of less than 1 second (i.e. a frequency greater than 1 Hz).

By way of example, step a) is carried out by the injection of oxygen at a flow rate comprised between 100 and 1000 sccm (standard cubic centimeters per minute), preferably between 100 and 500 sccm, for example 300 sccm.

The chemical species adapted to volatilize the oxidized metallic deposit can comprise hexafluoroacetylacetone (hfacH)

The hfacH species are injected in step b) according to a sequence of pulses having a period of 1 second, the duration of each pulse being 100 ms. During each pulse of the period of pulses, the hfacH species are injected according to a flow rate comprised between 100 and 500 sccm, for example 200 sccm.

The temperature in the deposition chamber is maintained at 50° C.

Thus, when the metallic deposit 2 comprises copper (Cu), the oxidation reactions of step a) are the following:

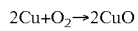

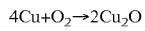

During a pulse of the sequence of pulses, the oxidation in step a) becomes in the minority, and the oxidized metallic deposit is volatilized by the hfacH species injected in step b) according to the following reactions:

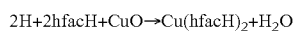

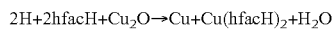

The remainder of the description presents two applications in which the removal method is implemented. The characteristics described above with reference to the removal method can be transposed to these two applications.

In a first application of the invention, the removal method is implemented for cleaning off metallic residues 2 disposed on the inner walls of a deposition chamber 1.

In this first embodiment, the enclosure mentioned in the removal method is a deposition chamber 1. The deposition chamber 1 can be a deposition chamber for chemical vapor deposition (CVD), for physical vapour deposition (PVD), for plasma-enhanced chemical vapor deposition (PECVD), for atomic layer deposition (ALD).

During the deposition of a film on a substrate disposed on the support 5 of the deposition chamber 1, unwanted deposits of the material comprised in the film are observed on the surfaces in the deposition chamber 1, namely on the inner walls of the deposition chamber 1, as well as on the support 5.

In the course of deposition implemented in the chamber 1, said unwanted deposits of material accumulate on these surfaces, and are a significant source of contamination of the films formed on the substrates.

The films formed in these deposition chambers can be metallic films, and the deposits of materials comprised in said films observed on the inner walls of the deposition chamber 1 are called metallic residues 2.

The invention then consists of cleaning off these metallic residues 2 placed on the inner walls of the deposition chamber 1. Similarly to the method for removing a metallic deposit described above, the method according to the first embodiment comprises the following steps:

a) a step of oxidizing the metallic residues 2;
b) a step of injecting chemical species adapted to volatilize the oxidized metallic residues.

Step b) is implemented during at least a part of step a). In step b), the chemical species are injected according to a sequence of pulses.

Figure 3:
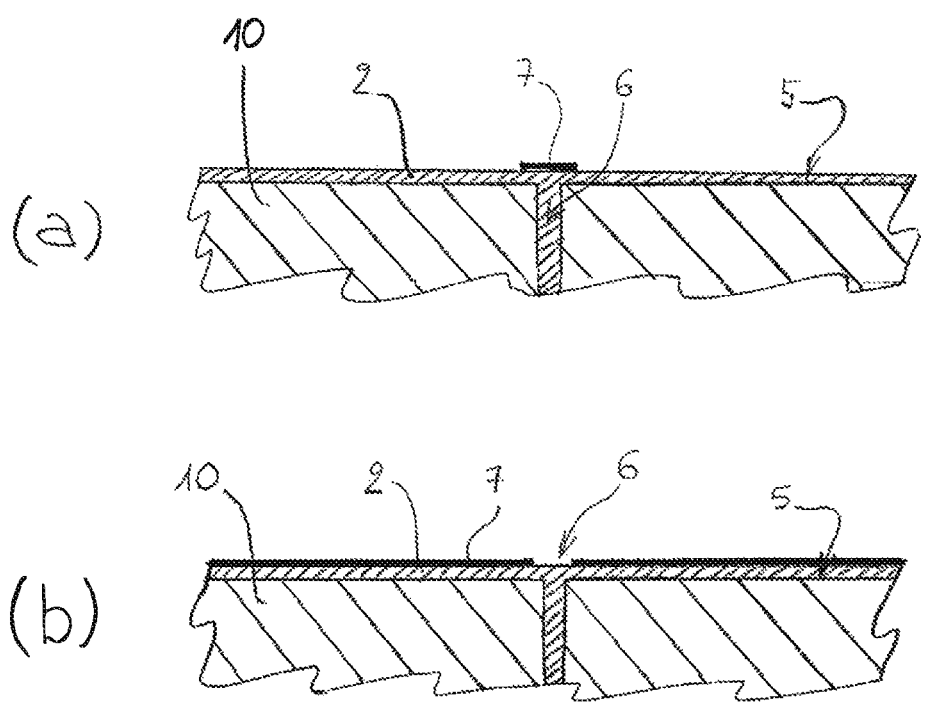
FIGS. 3(a) and 3(b) are partial transversal cross-sections of a printed circuit, the method of the invention being implemented according to two variants for etching a metallic deposit deposited in excess on the surface of a substrate of the printed circuit.

FIGS. 3(*a*) and 3(*b*) show two variants of a second application of the invention, in which the method for removing a metallic deposit 2 is implemented for the manufacturing a printed circuit 10, in order to etch a metallic deposit 2 deposited on a substrate of the printed circuit.

In the example of FIGS. 3(*a*) and 3(*b*), the metallic deposit 2 is used to fill a via 6. The vias 6 are metalized holes which allow the electrical connection between one or more layers of a printed circuit substrate.

In FIGS. 3(*a*) and 3(*b*), a single via 6 is shown, it being understood that the printed circuit 10 can comprise several vias 6.

The method of the invention can also be implemented in a more general manner for etching a metallic deposit deposited on the surface of a substrate. For example, the method makes it possible to produce a bump contact on a printed circuit substrate, starting from a layer of metallic deposit.

The substrate of the printed circuit 10 shown in FIGS. 3(*a*) and 3(*b*) comprises a face 5. A via 6 passes at least partially through the printed circuit 10 in order to electrically connect the face 5 to another layer of the printed circuit 10, not shown.

The metallic deposit 2 is produced in excess. It fills the via 6 in order to satisfactorily metalize it, and also covers the face 5 of the printed circuit 10. The method of the invention makes it possible to etch this excess metallic deposit 2, so that the metallic deposit only remains inside the via 6 and optionally protrudes externally, along its longitudinal axis. Around the via 6 and on the surface 5, the metallic deposit 2 is removed using the method of the invention.

The printed circuit 10 is placed in an enclosure (not shown), for example a deposition chamber similar to the deposition chamber 1 described with reference to the first application of the method of the invention, for cleaning off metallic residues.

FIG. 3(a) shows a first variant of the second embodiment. Before implementing the method, a mask 7 is affixed over each region of the metallic deposit 2 to be retained, at the level of the surface 5 of the printed circuit 10. The mask 7 is centred on the longitudinal axis of the via 6.

Then, steps a) and b) of the method are implemented according to the invention, in order to remove the excess metallic deposit 2 in each region of the surface 5 not covered by the mask 7.

During step a), the metallic deposit 2 is oxidized only around the via 6, as the mask 7 protects the via 6. At the end of step a), the part of the metallic deposit 2 situated in the via 6 and along its longitudinal axis is not oxidized.

During step b), chemical species adapted to volatilize the oxidized metallic deposit 2 are injected into the enclosure 1. Step b) is implemented during at least a part of step a). In step b), the chemical species are injected according to a sequence of pulses.

The chemical species adapted to volatilize the oxidized metallic deposit 2 act only around the via 6, the mask 7 protecting the metallic deposit 2 at the level of the via 6.

Steps a) and b) are repeated as many times as necessary in order to progressively remove the thickness of the excess part of the metallic deposit 2.

FIG. 3(b) shows a second variant of the second embodiment. Before implementing the method, a mask 7 is affixed over each region of the metallic deposit 2 to be etched, at the level of the surface 5 of the printed circuit 10 and around the via 6.

Then, chemical species adapted to passivate the metallic deposit 2 in each region not covered by the mask are injected into the enclosure 1. The passivation can be carried out by injecting, in excess with respect to the quantity of the metallic deposit, the oxidizing species and/or the chemical species adapted to volatilize the oxidized metallic deposit 2, preferably in an over-stoichiometric quantity with respect to the quantity of the metallic deposit 2.

Thus, the metallic deposit 2 is passivated only in the zones that are not masked, i.e. at the level of the via 6.

The mask 7 is then removed.

Then, steps a) and b) of the method are implemented according to the invention, in order to remove the excess metallic deposit 2 on the surface 5, in each region covered beforehand by the mask.

During step a), the metallic deposit 2 is oxidized only around the via 6, as at the level of the via 6, the metallic deposit is passivated and thus fulfills a mask function. At the end of step a), the metallic deposit is not oxidized at the level of the via 6.

During step b), chemical species adapted to volatilize the metallic deposit 2 are injected into the enclosure 1. Step b) is implemented during at least a part of step a). In step b), the chemical species are injected according to a sequence of pulses.

The chemical species capable of volatilizing the oxidized metallic deposit 2 act only around the via 6, the passivation protecting the metallic deposit 2 at the level of the via 6 in the manner of a mask.

Steps a) and b) are repeated as many times as necessary in order to remove the excess metallic deposit 2.

Compared with the conventional method for etching a metallic deposit by chemical mechanical polishing, the invention has the following advantages:

while mechanical-chemical polishing requires the deposition of a thick metallic layer (typically greater than or equal to 1.5 µm) in order to ensure the uniformity of the subsequent polishing, the etching implemented in the invention makes it possible to deposit only the thickness of metal sufficient for filling the via, i.e. a few hundreds of nanometers deposited in excess. The invention therefore makes it possible to reduce the quantity of metal to be deposited by approximately a factor of 10.

by not having to use mechanical-chemical polishing which leads to significant contamination of the substrate, the invention also avoids the cleaning steps consequent on this polishing, finally, the formation of a barrier layer between the substrate and the metallic deposit is no longer necessary.

Thus, using the invention, the etching of a metallic deposit deposited on a surface is simplified and less expensive.

Of course, the invention is not limited to the embodiments described. Variant embodiments can be made without exceeding the scope of the invention.

Thus, the method for removing a metallic deposit according to the invention makes it possible to limit the parasitic reactions capable of blocking said method.

REFERENCES

G. Zhou et al.: Initial oxidation kinetics of Cu(100), (110), and (111) thin films investigated by in situ UHV TEM, J. Mater. Res., Vol. 20, No. 7, July 2005

The invention claimed is:

1. A method for removing a copper deposit disposed on a surface in an enclosure, said method comprising the following steps:
   a. a step of flowing oxidizing species capable of oxidizing the copper deposit; and
   b. a step of flowing chemical species capable of volatilizing the oxidized copper deposit, said step b) being implemented during at least a part of said step a); and in step b), the chemical species are flowing according to a sequence of pulses;
   wherein during a first pulse of the sequence of pulses the oxidation of said step a) becomes a minority reaction and the oxidized copper deposit is volatized by the chemical species flowing in said step b); and
   wherein once said first pulse of the sequence of pulses has ended, the oxidation of the copper deposit is a dominant reaction until a next pulse of the sequence of pulses of said step b).

2. The method according to claim 1, wherein in step b), during a latest pulse of two successive pulses, the chemical species are flowing in a sub-stoichiometric quantity with respect to a quantity of the oxidized copper deposit between said two successive pulses.

3. The method according to claim 1, wherein the duration of the pulses of the sequence of pulses is set so that the layer of the oxidized copper deposit is not entirely oxidized.

4. The method according to claim 3, wherein two successive pulses are separated by a time interval during which no chemical species adapted to volatize the oxidized copper deposit is injected.

5. The method according to claim 1, wherein the chemical species flowing in step b) comprise hexafluoroacetylacetone.

6. The method according to claim 1, wherein the first pulse of step b) is implemented after the start of step a).

7. The method according to claim 1, wherein the method is implemented for cleaning off copper residues disposed on the inner walls of a deposition chamber.

8. The method according to claim 1, wherein the method is implemented for etching a copper deposit deposited in excess on a surface.

9. The method according to claim 8, wherein before steps a) and b), a mask is affixed in a localized manner onto the copper deposit.

10. The method according to claim 9, further comprising the following steps:
- the mask is affixed over each region of the copper deposit to be retained;
- steps a) and b) are implemented in order to remove the excess copper deposit in each region not covered by the mask.

11. The method according to claim 9, further comprising the following steps:
- the mask is affixed over each region of the copper deposit to be etched;
- flowing chemical species adapted to passivate the copper deposit in each region not covered by the mask;
- the mask is removed; and
- steps a) and b) are implemented in order to remove the excess copper deposit in each region covered beforehand by the mask.

12. The method according to claim 8, wherein steps a) and b) are repeated as many times as necessary in order to remove the excess copper deposit.

13. The method according to claim 1, wherein the oxidizing species consisting of a gaseous source.

14. The method according to claim 1, wherein the oxidizing species are continuously flowing throughout the removal of the copper deposit.

15. The method according to claim 14, wherein the oxidizing species are flowing at a constant flow rate throughout the removal of the copper deposit.

* * * * *